United States Patent [19]

Fischer et al.

[11] 4,104,462
[45] Aug. 1, 1978

[54] CARDIOACTIVE ADENOSINE NITRATES

[75] Inventors: Ulf Fischer, Frankendorf; Günther Haüsler, Reinach, both of Switzerland

[73] Assignee: Hoffmann-La Roche Inc., Nutley, N.J.

[21] Appl. No.: 813,200

[22] Filed: Jul. 5, 1977

Related U.S. Application Data

[63] Continuation of Ser. No. 654,510, Feb. 2, 1976, abandoned.

[30] Foreign Application Priority Data

Feb. 18, 1975 [CH] Switzerland ............................ 2032/75
Jul. 4, 1975 [CH] Switzerland ............................ 8748/75
Dec. 11, 1975 [CH] Switzerland ............................ 16094/75

[51] Int. Cl.² .................... C07H 19/16; C07H 19/18

[52] U.S. Cl. .................................... 536/26; 424/180; 536/24; 536/115

[58] Field of Search ............................. 536/24, 26

[56] References Cited

U.S. PATENT DOCUMENTS

| | | | |
|---|---|---|---|
| 3,832,341 | 8/1974 | Duschinsky | 536/26 |
| 3,855,205 | 12/1974 | Prasad et al. | 536/26 |
| 3,864,483 | 2/1975 | Stein et al. | 536/26 |

Primary Examiner—Johnnie R. Brown
Assistant Examiner—Blondel Hazel
Attorney, Agent, or Firm—Samuel L. Welt; George M. Gould

[57] ABSTRACT

The present disclosure relates to adenosine nitrates having cardiac activity.

23 Claims, No Drawings

CARDIOACTIVE ADENOSINE NITRATES

This is a continuation of U.S. patent application Ser. No. 654,510 filed Feb. 2, 1976, now abandoned.

DESCRIPTION OF THE INVENTION

The adenosine nitrates provided by the present invention are compounds of the formula

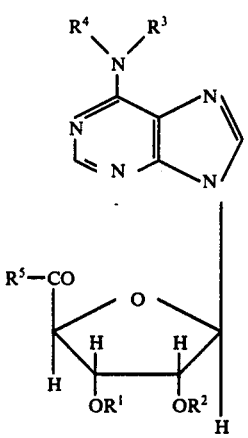

(I)

wherein $R^1$ and $R^2$ each independently is hydrogen, acyl or nitro with at least one of $R^1$ and $R^2$ being nitro; $R^3$ and $R^4$ each independently are hydrogen or acyl or $R^3$ and $R^4$ together are a diacyl residue of an aliphatic or aromatic dicarboxylic acid, and $R^5$ is hydroxy, lower alkoxy, amino, (lower alkyl)amino, di(lower alkyl)amino or cycloalkylamino group or a nitrogen-containing heterocyclic ring which is bonded via a nitrogen atom, and pharmaceutically acceptable acid addition salts thereof.

Sub-groups of compounds of formula I have the formulae I-1, I-2 and I-3.

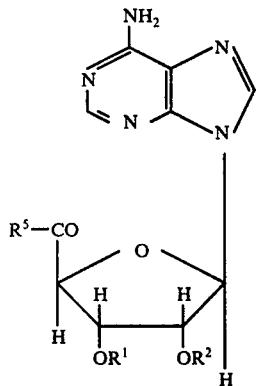

(I-1)

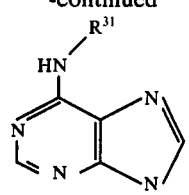

(I-2)

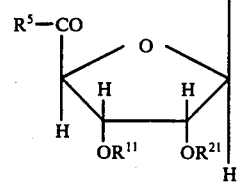

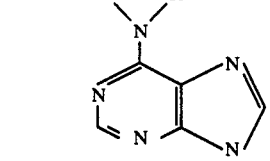

(I-3)

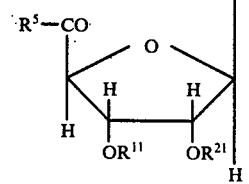

wherein $R^1$, $R^2$ and $R^5$ have the significance given earlier; $R^{11}$ and $R^{21}$ each independently is acyl or nitro with at least one of $R^{11}$ and $R^{21}$ being nitro; and, $R^{31}$ and $R^{41}$ each represent an acyl residue or $R^{31}$ and $R^{41}$ each represent an acyl residue or $R^{31}$ and $R^{41}$ together represent a diacyl residue of an aliphatic or aromatic dicarboxylic acid.

In this specification, the expressions "lower alkyl" and "lower alkoxy" include straight-chain or branched-chain groups containing 1-6 carbon atoms (E.G., methyl, methoxy, ethyl, ethoxy, propyl, propoxy, isopropyl, isopropoxy, sec.butyl, sec.butoxy, tert.butyl and tert.butoxy). The expression "acyl" means a residue of an aliphatic or aromatic, optionally-substituted monocarboxylic acid containing 2–10 carbon atoms (e.g., ethoxycarbonyl, acetyl, propionyl, butyryl, isovaleryl, pivaloyl, acryloyl, propiolyl, methacryloyl, crotonoyl, benzoyl, toluoyl, hydratropoyl and cinnamoyl). Diacyl residues of aliphatic acids can contain 4–10 carbon atoms, (e.g., succinyl, glutaryl, adipoyl, maleoyl and citraconoyl. Examples of (lower alkyl)amino and di(-lower alkyl)amino groups are methylamino, ethylamino, propylamino, butylamino, dimethylamino, diethylamino, and diisopropylamino). Examples of aryl(lower alkyl)amino groups, of which the phenyl-(lower alkyl)-amino groups are preferred, are the benzylamino and 1- and 2-phenethylamino groups. The cycloalkylamino groups are especially those which contain up to 7 carbon atoms (e.g., cyclopentylamino and cyclohexylamino). The nitrogen-containing heterocyclic ring which is bonded via a nitrogen atom can contain, in addition to at least one nitrogen atom, other hetero atoms such as oxygen or sulphur. Five-membered and six-membered heterocyclic rings are preferred. Examples of such rings are aziridino, azetidino, pyrrolidino, pyrrolo, imidazolidino, pyrazolino, thiazolino, thiazolidino, piperidino, morpholino and azepino.

Among pharmaceutically acceptable acid addition salts, are salts of compounds of formula I with suitable organic or inorganic acids such as hydrochlorides, hydrobromides, sulphates, bisulphates, phosphates, acetates, lactates, oleates, nitrates, mesylates, tosylates, citrates, maleates, succinates, tartrates, etc.

According to the process provided by the present invention, the adenosine nitrates aforesaid (i.e., the compounds of formula I and their pharmaceutically acceptable acid addition salts are prepared by nitrating and optionally O- and/or N-acylating a compound of the formula

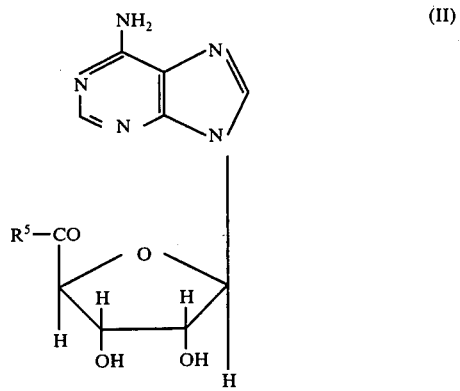

wherein $R^5$ has the significance given earlier, and, if desired, converting the product into a pharmaceutically acceptable acid addition salt.

The nitration and acylation of a compound of formula II can be carried out according to methods known per se.

Thus, the nitrogen can be carried out, for example, using nitric acid. Hydrolysis (by water formed in the reaction) or deamination (by nitrous acid which may be present) is expediently suppressed by the addition of a water-binding agent such as concentrated sulphuric acid, oleum, phosphorus pentoxide, acetic anhydride and/or a nitrite acceptor such as urea.

The nitration is expediently carried out at low temperatures, preferably at $-30°$ C. to 25° C. and especially at $-10°$ C. to 0° C.

There are usually obtained mixtures of the 2'-O-nitro, 3'-O-nitro and 2',3'-di-O-nitro compounds in question, which mixtures can be separated according to generally known methods (e.g., chromatograph) and worked-up to give the pure compounds. It is however, also possible to control the process so that the 2',3'-di-O-nitro compounds are isolated as the sole products, which is predominantly the case when oleum is used.

The acylation of the nitro compounds can likewise be carried out in a manner known per se by reaction with a reactive acid derivative such as, for example, an acyl halide or acid anhydride such as acetyl chloride, benzoyl chloride or acetic anhydride or an activated ester or a ketene. In this case, the hydroxyl groups of the sugar residue are preferably esterified. The selective O-acylation is favoured by relatively low temperatures and short acylation times. With higher temperatures and a longer acylation time, the amino group present in the 6-position is then also acylated, firstly to the monacyl derivative and then to the diacyl derivative. There is generally obtained as the product a mixture of mono-, di- and/or triacyl derivatives which can be separated in the usual manner.

The conversion of the compounds of formula I into pharmaceutically acceptable acid addition salts as well as the formation of such salts from acid addition salts which are not physiologically acceptable can be carried out in the usual manner.

The compounds of formula I and their physiologically acceptable acid addition salts possess valuable effects on the heart and on the cirulatory-dynamics and can accordingly be used as medicaments, inter alia, for the treatment of angina pectoris or essential hypertonia. As dosage guidelines, an amount of 0.010–30 mg/kg body weight per day can be considered. Such dosage can be administered not only as a single dose but preferably several times daily in divided doses.

The coronary-dilating activity can be measured according to the following method:

Mongrels weighing between 20 and 38 kg are used for the examinations. The test animals are anaesthetized with ca 30 mg/kg i.v. pentobarbital. The anaesthesia is maintained with chloralose-urethane. The animals are artificially respired with room air. After opening the thorax, the heart is exposed and a previously calibrated flow probe of an electromagnetic flow-meter is placed around the circumflex branch of the left coronary artery for measurement of coronary blood flow. The arterial blood pressure is measured via a catheter in the femoral astery with a pressure transducer. Further, a calibrated strain gauge is sutured to the surface of the left ventricle for the measurement of myocardial contractile force. The pulse wave of the blood pressure triggers a tachograph for the measurement of the heart rate. The compounds are dissolved in propylene glycol and administered either intravenously or intraduodenally as a suspension in gum arabic. The maximum action of a substance is calculated in percent of the starting value according to each dosage. In the measurement of the coronary blood flow, special attention is paid to the duration of action.

The results obtained are compiled in the following Table in which $n$ signifies the number of animals used.

Table

| Compound | n | Dose i.v. [mg/kg] | BP Δ% | BP [min] | HR Δ% | HR [min] | CF Δ% | CF [min] | CABF Δ% | CABF [min] |
|---|---|---|---|---|---|---|---|---|---|---|
| 2',3'-Di-O-nitroadenosine-5'-carboxylic acid ethyl ester | 2 | 3.0 | −45 | 31 | +8.5 | >2 | −27 | >27 | +356 | 21 |
| 2'-O-Nitroadenosine-5'-carboxylic acid ethyl ester | 2 | 1.0 | −14 | 27 | +2.5 | >2 | — | | +244 | 30 |
| | | 3.0 | −49 | 50 | +2.5 | -O-Nitroadenoisine-5'2 | — | | +412 | 67 |

Table-continued

| Compound | n | Dose i.v. [mg/kg] | BP Δ% | [min] | HR Δ% | [min] | CF Δ% | [min] | CABF Δ% | [min] |
|---|---|---|---|---|---|---|---|---|---|---|
| 2'-O- carboxylic acid ethylamide | 3 | 0.01 | −38 | 120 | 0 | 120 | — | | +115 | 120 |

BP = Arterial Blood Pressure
HR = Heart Rate
CF = Cardiac Contractile Force
CABF = Coronary Flow The adenosine nitrates provided by the present invention can be used as medicaments in the form of pharmaceutical preparations, having direct or delayed release of the active ingredient, which contain them in association with a compatible pharmaceutical carrier material. This carrier material can be an organic or inorganic inert carrier material suitable for enteral, percutaneous or parenteral administration such as, for example, water, gelatin, gum arabic, lactose, starch, magnesium stearate, talc, vegetable oils, polyalkyleneglycols, petroleum jelly etc. The pharmaceutical preparations can be made up in a solid form (e.g. as tablets, dragées, suppositories or capsules), in a semi-solid form (e.g. as salves) or in a liquid form (e.g. as solutions, suspensions or emulsions). The pharmaceutical preparations may be sterilised and/or may contain adjuvants such as preservatives, stabilisers, wetting agents, emulsifiers, flavour-improving agents, salts for varying the osmotic pressure or buffers. The pharmaceutical preparations can be prepared in a manner known per se.

The starting materials of formula II hereinbefore are known or can be prepared from known compounds in a manner known per se.

The following Examples illustrate the process provided by the present invention:

EXAMPLE 1

6.7 g of urea were slowly added at −15° C to 90 ml of fuming nitric acid ($d = 1.5$) at such a rate that the temperature did not exceed −10° C. To this solution there were added successively at −10° C 10.8 g of adenosine-5'-carboxylic acid ethyl ester. The solution was stirred for 3 hours in an ice-bath, introduced into a mixture of 225 g of potassium bicarbonate and 1000 g of ice-water and the precipitated crude product (4.4. g) was filtered off under suction. By extraction of the filtrate with chloroform/methanol (95:5), there were obtained a further 4.4 g of the crude product which, by chromatography on silica gel with chloroform/ethyl acetate/methanol (45:45:10), yielded the following nitroadenosines:

2.65 g of 2',3'-di-O-nitroadenosine-5'-carboxylic acid ethyl ester of melting point greater than 135° C (decomposition) (from ethyl acetate/chloroform);

0.41 g of 2'-nitroadenosine-5'-carboxylic acid ethyl ester of melting point 170°–171° C (decomposition) (from ethyl acetate/diethyl ether);

1.3 g of 3'-O-nitroadenosine-5'-carboxylic acid ethyl ester of melting point 166.5°–167° C (decomposition) (from ethanol).

EXAMPLE 2

100 ml of fuming nitric acid ($d = 1.50$) were cautiously treated at −20° C with 6.7 g of urea. 10.8 g of adenosine-5'-ethylamide were dissolved in this solution, the temperature being maintained at −20° C. The mixture was subsequently stirred firstly at −20° C, then slowly warmed to −5° C and, after a total of 5 hours, introduced slowly into excess aqueous potassium bicarbonate solution (230 g of potassium bicarbonate in 800 ml of water). After filtering under suction and washing the precipitate with water, the filtrate was extracted five times, each time with 400 ml of a mixture of ethyl acetate and 5% tetrahydrofuran. The organic phases were washed with saturated sodium chloride solution, dried over magnesium sulphate and concentrated under reduced pressure. The total yield of crude product amounted to 11.5 g.

In order to separate the crude product into the 3 nitrate esters, it was recrystallised several times from ethanol, there being obtained pure 3'-O-nitroadenosin-5'-ethylamide. 2',3'-Di-O-nitroadenosin-5'-ethylamide could be obtained from the mother liquors by crystallisation from acetonitrile, while the complete separation of the mother liquors by chromatography on silica gel with chloroform/methanol/glacial acetic acid (90:10:1, v/v) also yielded 2'-O-nitroadenosine-5'-carboxylic acid ethylamide.

The total yields were:

3.0 g (24%) of 3'-O-nitroadenosine-5'-carboxylic acid ethylamide of melting point 210° C (decomposition) (from ethanol);

2.5 g (17.8%) of 2',3'-di-O-nitroadenosine-5'-carboxylic acid ethylamide of melting point 164° C (decomposition) (from acetonitrile) and 0.77 g (6.2%) of 2'-O-nitroadenosine-5'-carboxylic acid ethylamide of melting point 208° C (decomposition) (from ethanol).

EXAMPLE 3

72 ml of fuming nitric acid were cautiously treated at −20° C with 4.9 g of urea. 6.9 g of adenosine-5'-carboxylic acid amide were slowly introduced into this solution, care being taken that the temperature of the mixture did not rise above −15° C. The mixture was stirred for a further 5 hours while cooling to at least −5° C and then slowly added dropwise into excess aqueous potassium bicarbonate solution (175 g of potassium bicarbonate in 500 ml of water), whereby a portion of the product precipitated. After filtering under suction and washing with water, there were obtained 2.9 g of a mixture of 2',3'-di-O-nitroadenosine-5'-carboxylic acid amide and 3'-O-nitroadenosine-5'-carboxylic acid amide. The aqueous solution was extracted three times with 150 ml of chloroform and 5% ethanol each time and subsequently three times with 150 ml of ethyl acetate and 5% tetrahydrofuran each time. After washing with saturated sodium chloride solution and drying over magnesium sulphate, there were obtained, after concentration of the chloroform/ethanol extract, 2.0 g of almost pure 2',3'-di-O-nitroadenosine-5'-carboxylic acid amide and, from the ethyl acetate/tetrahydrofuran extract, 5.7 g of a mixture of 3'-O-nitroadenosine-5'-carboxylic acid amide and 2'-O-nitroadenosine-5'-carboxylic acid amide. Repeated recrystallisation of the residue obtained from the chloroform/ethanol extract gave 1.17 g (12.8%) of pure 2',3'-di-O-nitro-adenosine-5'-carboxylic acid amide of melting point 172.5° C (decomposition). Repeated recrystallisation of the residue obtained from the ethyl acetate/tetrahydrofuran extract from ethanol/isopropanol and subsequently from methanol/water gave 2.25 g (28.1%) of 3'-O-nitroadenosine-5'-carboxylic acid amide of melting point 211° C (decomposition).

EXAMPLE 4

6.16 g of adenosine-5'-carboxylic acid dimethylamide were dissolved at −40° C in 60 ml of fuming nitric acid ($d = 1.50$). A mixture, cooled to −20° C, of 30 ml of oleum and 30 ml of nitromethane was added dropwise to this solution within 30 minutes at such a rate that the temperature did not rise above −30° C. The mixture was stirred for 45 minutes at a temperature between −30° C and −25° C and then poured on to a solution of 325 g of potassium bicarbonate in 1 liter of water. By extraction with chloroform or with chloroform containing 5% n-propanol, there was obtained practically pure 2',3'-di-O-nitroadenosine-5'-carboxylic acid dimethylamide which melted at 156.5° C (decomposition) after recrystallisation from alcohol. The yield was 5.78 g (72.7% of theory).

In an analogous manner, the following 2',3'-di-O-nitro-adenosines were obtained:

2',3'-di-O-nitroadenosine-5'-carboxylic acid isopropyl-amide of melting point 183° C (decomposition), yield 77.4%;

2',3'-di-O-nitroadenosine-5'-carboxylic acid cyclohexylamide of melting point 168° C (decomposition), yield 69.5%;

2',3'-di-O-nitroadenosine-5'-carboxylic acid [2-(dimethyl-amino)-ethyl]-amide of melting point 169° C (decomposition), yield 63%;

2',3'-di-O-nitroadenosine-5'-carboxylic acid [2-(2,4-dinitrophenyl)-ethyl]-amide of melting point 134° C (decomposition), yield 30.6%;

2',3'-di-O-nitroadenosine-5'-carboxylic acid piperidide of melting point 160° C (decomposition), yield 76.2%;

2',3'-di-O-nitroadenosine-5'-carboxylic acid [2-(nitrooxy)-ethyl]-amide of melting point 164° C (decomposition), yield 58.9%;

2',3'-di-O-nitroadenosine-5'-carboxylic acid isopropyl ester of melting point 158° C (decomposition), yield 71.6%.

EXAMPLE 5

The reaction of 6.16 g of adenosine-5'-carboxylic acid dimethylamide with 60 ml of fuming nitric acid and working-up in the manner described in Example 4, but without the addition of oleum/nitromethane, yielded a mixture of 3'-O-nitroadenosine-5'-carboxylic acid dimethylamide of melting point 214° C (decomposition), yield 21% of theory, with 2',3'-di-O-nitroadenosine-5'-carboxylic acid dimethylamide of melting point 156° C (decomposition), yield 9.3% of theory.

We claim:

1. A compound of the formula

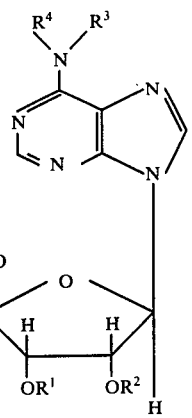

wherein $R^1$ and $R^2$ each independently is hydrogen, or nitro with at least one of $R^1$ and $R^2$ being nitro; $R^3$ and $R^4$ each independently is hydrogen and $R^5$ is hydroxy, lower alkoxy, amino, (lower alkyl)-amino, di(lower alkyl)amino, phenyl-(lower alkyl)-amino, a cycloalkylamino group selected from cyclopentylamino and cyclohexylamino, 2-(dimethylamino)-ethylamino, 2(2,4-dinitrophenyl)-ethylamino, 2-(nitro-oxy)-ethylamino or a nitrogen-containing 5 or 6 membered heterocyclic ring which can contain another hetero atom selected from oxygen or sulphur which ring is bonded via a nitrogen atom and pharmaceutically acceptable acid addition salts thereof.

2. A compound of claim 1 of the formula

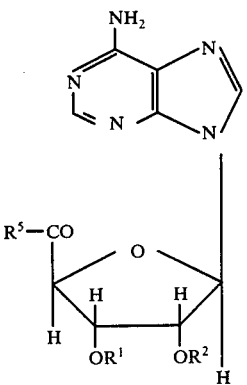

wherein $R^1$ and $R^2$ each independently is hydrogen, $C_2$-$C_{10}$ acyl or nitro with at least one of $R^1$ and $R^2$ being nitro, and $R^5$ is hydroxy, lower alkoxy, amino, (lower alkyl)amino, di(lower alkyl)amino, phenyl-(lower alkyl)-amino a cycloalkylamino selected from cyclopentylamino and cyclohexylamino or a nitrogen-containing 5 or 6 membered heterocyclic ring which can contain another hetero atom selected from oxygen or sulphur which is bonded via a nitrogen atom, and pharmaceutically acceptable acid addition salts thereof.

3. An adenosine nitrate of claim 2, wherein $R^5$ is hydroxy, lower alkoxy, amino, (lower alkyl)amino or di(lower alkyl)amino.

4. The compound of claim 3 which is 2',3'-di-O-nitroadenosine-5'-carboxylic acid ethyl ester.

5. The compound of claim 3 which is 2'-O-nitroadenosine-5'-carboxylic acid ethyl ester.

6. The compound of claim 3 which is 3'-O-nitroadenosine-5'-carboxylic acid ethyl ester.

7. The compound of claim 3 which is 2', 3'-di-O-nitroadenosine-5'-carboxylic acid ethylamide.

8. The compound of claim 3 which is 2'-O-nitroadenosine-5'-carboxylic acid ethylamide.

9. The compound of claim 3 which is 3'-O-nitroadenosine-5'-carboxylic acid ethylamide.

10. The compound of claim 3 which is 2', 3'-di-O-nitroadenosine-5'-carboxylic acid amide.

11. The compound of claim 3 which is 2'-O-nitroadenosine-5'-carboxylic acid amide.

12. The compound of claim 3 which is 3'-O-nitroadenosine-5'-carboxylic acid amide.

13. The compound of claim 3 which is 2', 3'-di-O-nitroadenosine-5'-carboxylic acid dimethylamide.

14. The compound of claim 3 which is 2', 3'-di-O-nitroadenosine-5'-carboxylic acid isopropylamide.

15. The compound of claim 2 which is 2', 3'-di-0-nitroadenosine-5'-carboxylic acid cyclohexylamide.

16. The compound of claim 2 which is 2', 3'-di-O-nitroadenosine-5'-carboxylic acid [2-(dimethylamino)-ethyl]-amide.

17. The compound of claim 2 which is 2', 3'-di-O-nitroadenosine-5-carboxylic acid [2-(2,4-dinitrophenyl)-ethyl]-amide.

18. The compound of claim 2 which is 2', 3'-di-O-nitroadenosine-5'-carboxylic acid piperidide.

19. The compound of claim 3 which is 2', 3'-di-O-nitroadenosine-5'-carboxylic acid [2-(nitro-oxy)-ethyl]-amide.

20. The compound of claim 3 which is 2',3'-di-O-nitroadenosine-5'-carboxylic acid isopropyl ester.

21. A compound of claim 1 of the formula

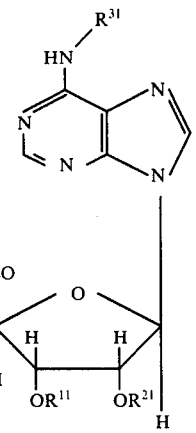

wherein $R^{11}$ and $R^{21}$ each independently is $C_2$–$C_{10}$ acyl or nitro with at least one of $R^{11}$ and $R^{21}$ being nitro; $R^{31}$ is $C_2$–$C_{10}$ acyl and $R^5$ is hydroxy, lower alkoxy, amino, (lower alkyl)-amino, di(lower alkyl)amino, phenyl (lower alkyl)amino a cycloalkylamino selected from cyclopentylamino and cyclohexylamino or a nitrogen-containing 5 or 6 membered heterocyclic ring which can contain another hetero atom selected from oxygen or sulphur which is bonded via a nitrogen atom, and pharmaceutically acceptable acid addition salts thereof.

22. An adenosine nitrate of claim 21, wherein $R^5$ is hydroxy, lower alkoxy, amino, (lower alkyl)amino or di(lower alkyl)amino.

23. A compound of claim 1 of the formula

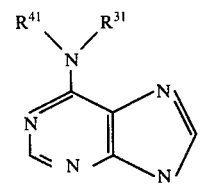

wherein $R^{11}$ and $R^{21}$ each independently is $C_2$–$C_{10}$ acyl or nitro with at least one of $R^{11}$ and $R^{21}$ being nitro; $R^{21}$ and $R^{42}$ each independently is $C_2$–$C_{10}$ acyl or $R^{31}$ and $R^{41}$ together are $C_4$–$C_{10}$ diacyl residue of an aliphatic or aromatic dicarboxylic acid and $R^5$ is hydroxy, lower alkoxy, amino, (lower alkyl)amino, di(lower alkyl)amino, phenyl (lower alkyl) amino a cycloalkylamino selected from cyclopentylamino and cyclohexylamino group or a nitrogen-containing 5 or 6 membered heterocyclic ring which can contain another hetero atom selected from oxygen or sulphur which is bonded via a nitrogen atom, and pharmaceutically acceptable acid addition salts thereof.

* * * * *